United States Patent
Lesner et al.

(10) Patent No.: US 10,556,925 B2
(45) Date of Patent: Feb. 11, 2020

(54) COMPOUND, PROCESS FOR ITS PREPARATION, A PHARMACEUTICAL SOLUTION CONTAINING THE COMPOUND, A METHOD OF DETERMINING THE PRESENCE OF CANCER, A KIT FOR CANCER DETECTION, AND THE USE OF HYDROLYSIS OF THE COMPOUND FOR THE DETECTION OF CANCER

(71) Applicant: INSTYTUT BIOTECHNOLOGII I MEDYCYNY MOLEKULARNEJ, Gdansk (PL)

(72) Inventors: Adam Lesner, Gdansk (PL); Magdalena Wysocka, Gdansk (PL); Dawid Nidzworski, Gdansk (PL)

(73) Assignee: INSTYTUT BIOTECHNOLOGII I MEDYCYNY MOLEKULARNEJ, Gdansk (PL)

( * ) Notice: Subject to any disclaimer, the term of this patent is extended or adjusted under 35 U.S.C. 154(b) by 0 days.

(21) Appl. No.: 16/082,032

(22) PCT Filed: Mar. 3, 2017

(86) PCT No.: PCT/PL2017/000018
§ 371 (c)(1),
(2) Date: Sep. 4, 2018

(87) PCT Pub. No.: WO2017/150997
PCT Pub. Date: Sep. 8, 2017

(65) Prior Publication Data
US 2019/0248835 A1 Aug. 15, 2019

(30) Foreign Application Priority Data
Mar. 4, 2016 (PL) .......................... 416395

(51) Int. Cl.
*C07K 5/02* (2006.01)
*C07K 5/11* (2006.01)
*G01N 33/574* (2006.01)
*G01N 33/58* (2006.01)

(52) U.S. Cl.
CPC ..... *C07K 5/1019* (2013.01); *G01N 33/57407* (2013.01); *G01N 33/582* (2013.01)

(58) Field of Classification Search
None
See application file for complete search history.

(56) References Cited

FOREIGN PATENT DOCUMENTS

WO 2015026251 2/2015

OTHER PUBLICATIONS

International Search Report and Written Opinion dated Jul. 21, 2017, from International Application No. PCT/PL2017/000018, 9 sheets.
Gruba Natalia et al.: Novel internally quenched substrate of the trypsin-like subunit of 20S eukaryotic proteasome. Analytical Biochemistry. 2015; 508: 38-45.
Borissenko L., Groll M., Diversity of proteasomal missions: fine tuning of the immune response. Biol. Chem. 2007; 388: 947-955.
Groll M., Bochtler M. et al., Molecular machines for protein degradation. ChemBioChem. 2005; 6: 222-256.
Ma W., Kantarjian H. et al., Enzymatic activity of circulating proteasomes correlates with clinical behavior in patients with chronic lymphocytic leukemia. Cancer 2008; 112(6):1306-12.
Ostrowska H. et al., Assessment of circulating proteasome chymotrypsin-like activity in plasma of patients with acute and chronic leukemias. Clin Biochem. 2008; 41(16-17):1377-83.
www.promega.com, 6 sheets.

*Primary Examiner* — Thomas S Heard
(74) *Attorney, Agent, or Firm* — Katten Muchin Rosenman LLP (57) ABSTRACT

The subject of the invention is a new compound of the following chemical formula:

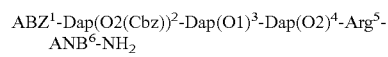

where: ABZ stands for 2-aminobenzoic acid; DAP stands for diaminopropanoic acid (Dap) derivatives, modified by the functionalised residues of mono-ethylene or diethylene glycol (PEG); ANB stands for 5-amino-2-nitrobenzoic acid The subject of the invention is a method for producing the new compound and a pharmaceutical solution for cancer detection, which contains the above-mentioned compound. The subject of the invention is a method for cancer detection through the in vitro analysis of a human urine sample to which a new compound is added and blended with a buffer of pH 7-9.

The subject of the invention is also a kit for detecting cancer, in particular bladder cancer, and the use of hydrolysis of the new compound in the position no. 5 by proteasome 20s for cancer detection, in particular bladder cancer.

12 Claims, 12 Drawing Sheets

COMPOUND, PROCESS FOR ITS PREPARATION, A PHARMACEUTICAL SOLUTION CONTAINING THE COMPOUND, A METHOD OF DETERMINING THE PRESENCE OF CANCER, A KIT FOR CANCER DETECTION, AND THE USE OF HYDROLYSIS OF THE COMPOUND FOR THE DETECTION OF CANCER

CROSS-REFERENCE TO RELATED APPLICATIONS

This application is a U.S. national phase application filed under 35 U.S.C. § 371 of International Patent Application No. PCT/PL2017/000018 filed Mar. 3, 2017, which in turn claims priority of Polish Patent Application No. P.416395, filed Mar. 4, 2016, the disclosures of each of which are hereby incorporated herein by reference in their respective entireties, for all purposes.

The subject of this invention is a new compound, the method for its production, a pharmaceutical solution which contains the new compound, a method for determining the presence of cancer, a cancer test kit and the use of hydrolysis of the new compound for cancer detection.

Solid-phase synthesis of peptides was first introduced in the 1980s by Bruce Merfield, who was awarded a Nobel Prize for his achievement.

Proteasome is a multi-catalytic complex of endopeptidase (EC 3.4.25.1), which is responsible for non-lysosomal removing of proteins which are damaged or incorrectly formed due to a mutation or external factors which cause oxidative stress. The compounds which have been examined until now and which enabled to denote the activity of proteasome 20S or 26S are short peptides which contain 4-5 amino acid residues. These amino acid residues contain a fluorescent group on the C-terminus. These compounds allow to determine the activity of proteasome, including the presence of proteasome or another proteolytic enzyme. When the C-terminus fluorescent group is released, it tends to be highly fluorescent Examples of sequences for such fluorogenic substrates are described in the work by Ma. This kind of compounds was used to indicate the activity of proteasome in plasma. Leu-Lcu-Val-Tyr-AMC, AMC is aminocoumarin.

The overview of literature indicates that the main subject of studies monitoring the level of proteasome activity are circulatory system cancers. The great majority of peptide derivatives which are proteasome substrates was described in laboratories like Promega or Molecular Probes. Alternatively, the measurement of proteasome concentration is performed using immunochemical techniques (ELISA tests), which are based on determining a particular proteasome subunit by a particular type of antibodies. However, this procedure is time-consuming and it leads to detecting the whole proteasome population, not its actively enzymatic fraction.

The examined and obtained compound, the marked peptide, is characterised by a high value of specificity constant (of $4.3 \times 10^6$ $M^{-1} \times s^{-1}$) and limits of determination and detection, proper for this kind of markings, which are 10 pM and 0.4 pM, respectively. These values are the evidence that the compound is hydrolysed by proteasome with high efficiency, moreover, even in the presence of 10 pM of this enzyme. The whole procedure of proteasome activity detection takes little time (30 minutes), is not a complex one (2 solutions need to be mixed), and little amount of an easily accessible biological material such as human urine is needed (the minimal volume is 50 µl). The basic advantage of the obtained compound and the method related to it is the possibility of diagnosing bladder cancer by using the procedure described below. A positive result (fluorescence growth in time) means that the urine contains active proteasome, and tins strongly correlates with the presence of cancer.

The P. 408905 invention revealed the new compound, whose hydrolysis in the position no. 5 by proteasome 20s is used to detect cancer, particularly bladder cancer. However, the compound claimed in this invention is more selective than the previous one, which means it is more cancer-sensitive (3.2 more times sensitive in the determination limit and 12.5 times more sensitive in detection). Moreover, it can detect smaller amounts of proteasome 20s. The new compound is a peptide, which means it is not degradable.

The aim of this invention is to provide a new compound and methods which could be used to diagnose cancer, especially bladder canoe-.

The subject of this application is the compound of the following formula: ABZ-Dap(O2(Cbz))-Dap(O1)-Dap(O2)-Arg-ANB-NH2, the method for its synthesis, and its use.

Figure 1:
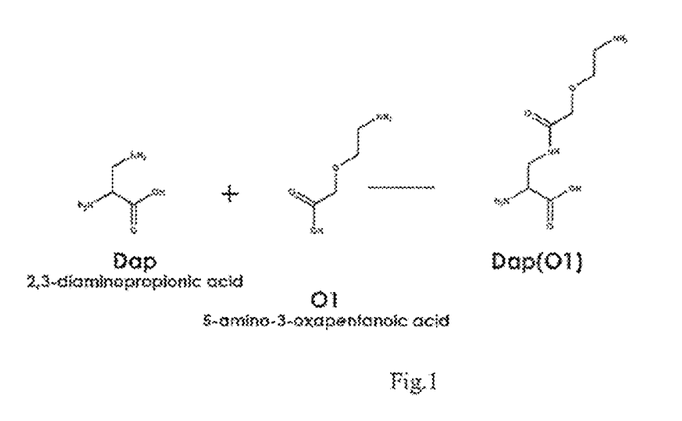
FIG. 1—it presents the synthesis of a sample DAPEG residue
Figure 2:
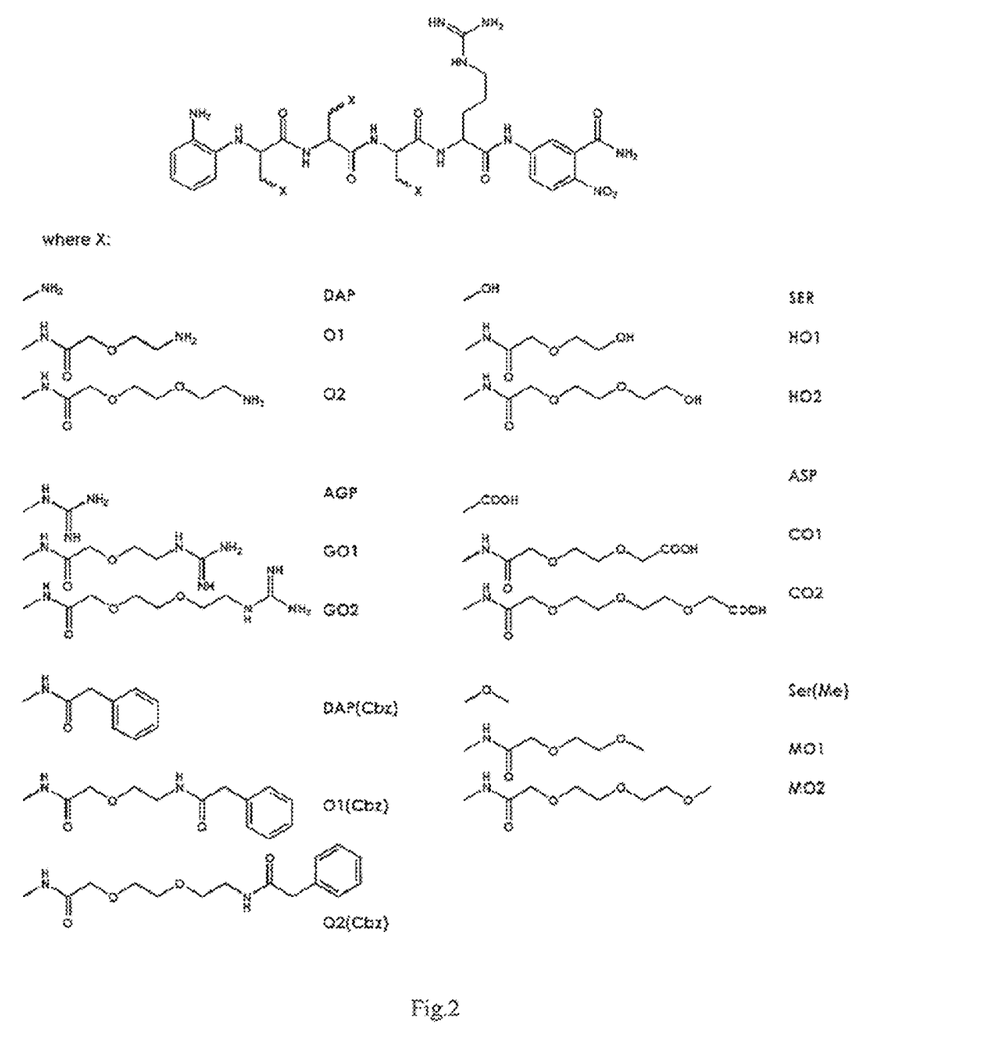
FIG. 2—it presents building blocks of the library which contain DAPEG residues.
Figure 3A:
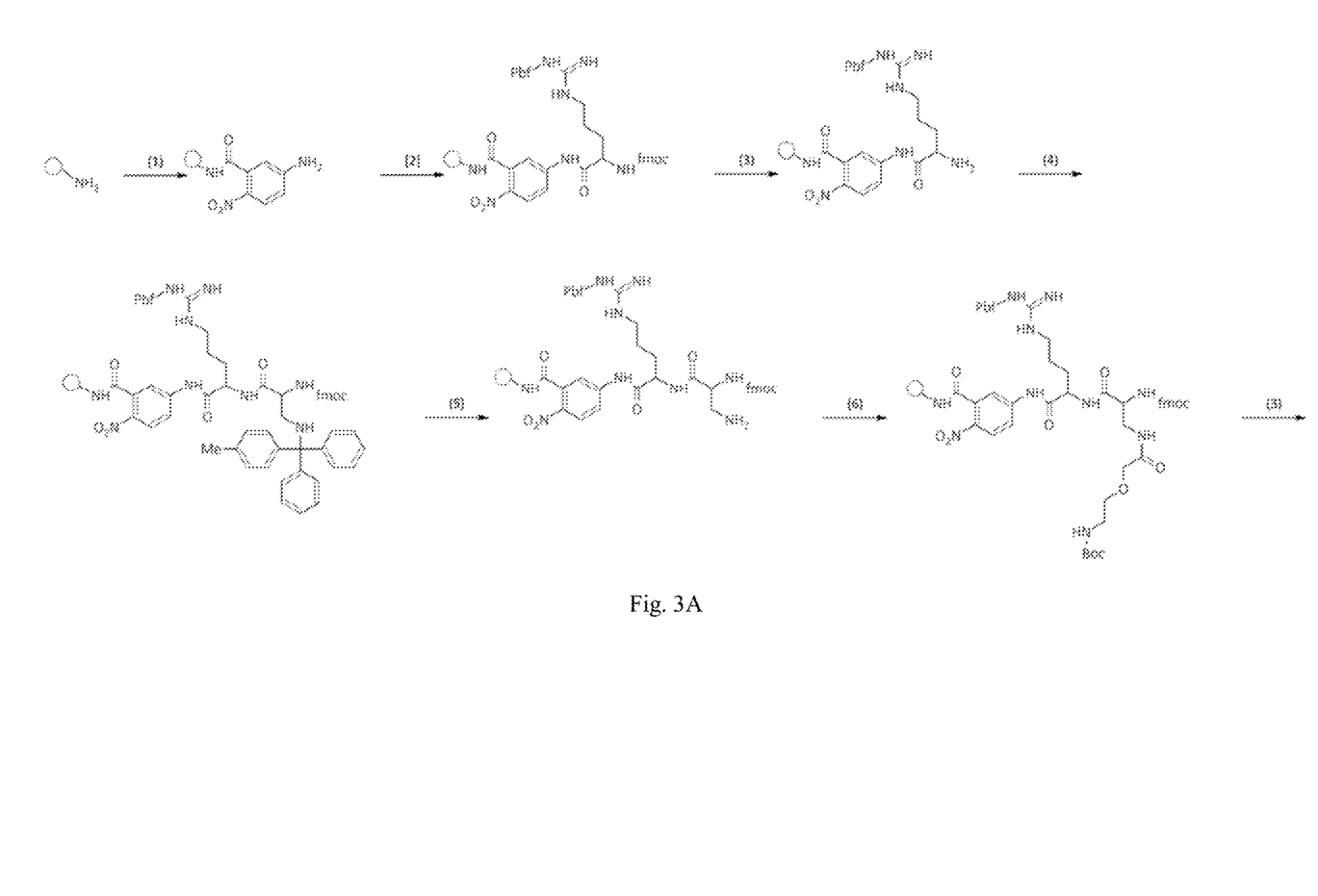
FIGS. 3A-3C—presents an example of a synthesis of a compound which contains DAPEG residues FIG. 4—it presents the chemical formula for the compound—a substrate selectively hydrolysed by trypsin-like subunit of proteasome 20S.
Figure 3B:
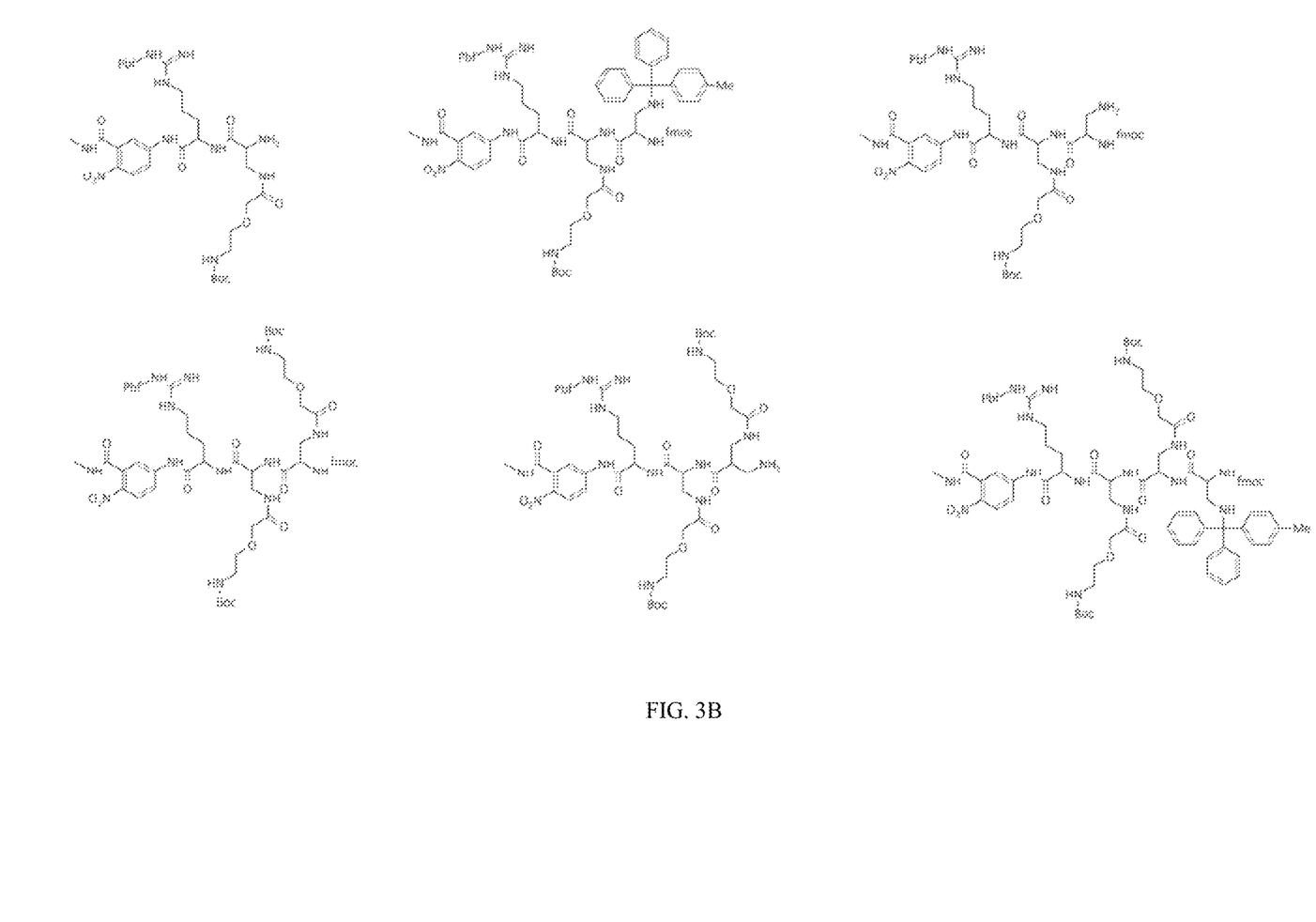
Figure 3C:
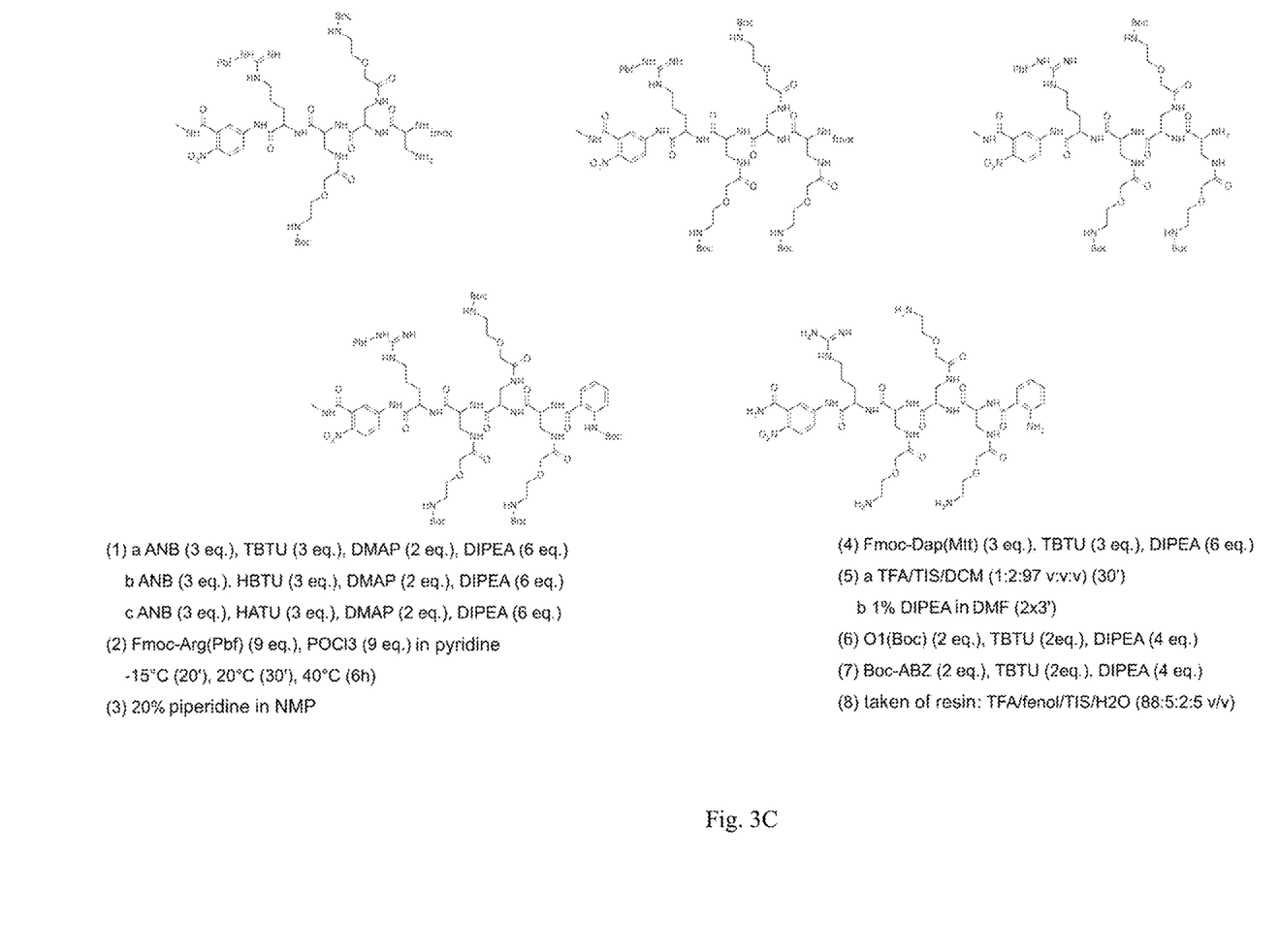
Figure 4:
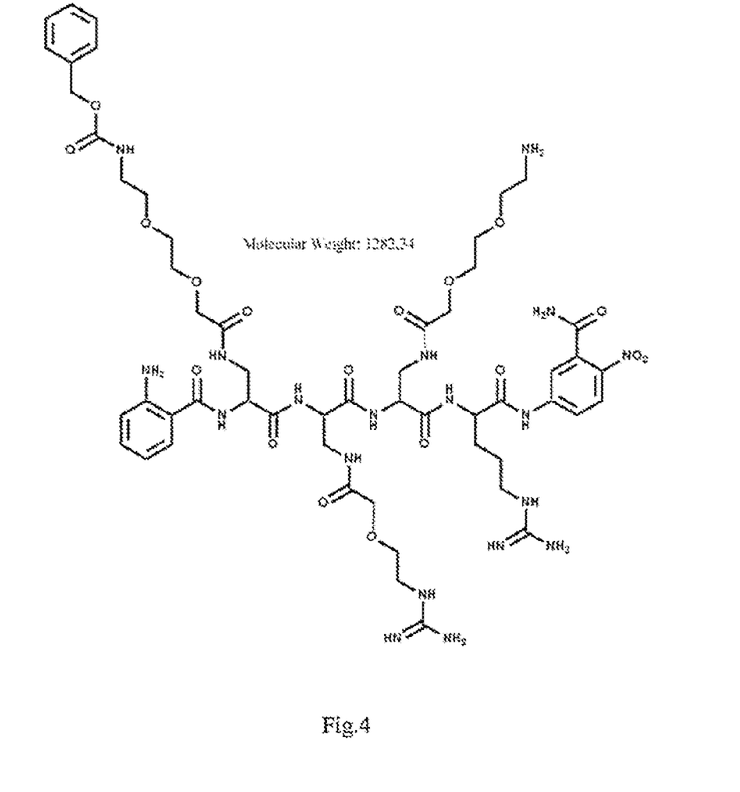
Figure 4A:
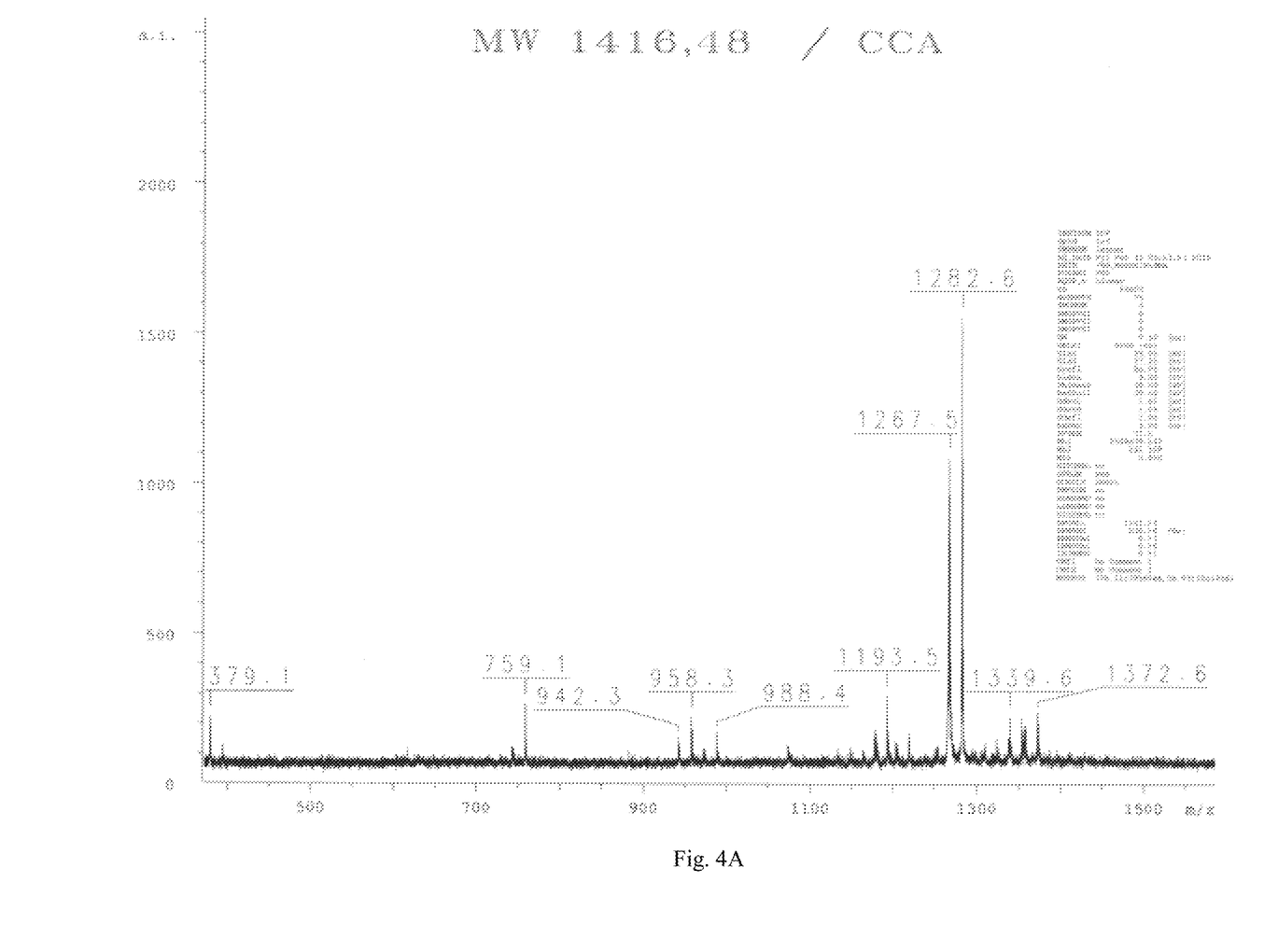
FIG. 4A—it presents the mass spectrum of the ABZ-Dap(O2(Cbz))-Dap(O1)-Dap(O2)Arg-ANB-NH$_2$ compound (molecular mass: 1283). 1282.6 ions (pseudo-molecular) and the fragment ion M-15 are present.

In the synthesis of this compound, new building blocks, which are derivatives of diamino adds (Dap), were used. They were modified by the functionalised residues of mono-ethylene or diethylene glycol (PEG) (their proposed general name is DAPEG (DAP-f PEG)). An example of their synthesis is shown in diagram 1.

The subject of this invention is a new compound of the following formula:

where:

ABZ stands for 2-aminobenzoic acid

DAP stands for diaminopropanoic add (Dap) derivatives, modified by the functionalised residues of mono-ethylene or diethylene glycol (PEG)

ANB stands for 5-amino-2-nitrobenzoic acid

Furthermore, the subject of this invention is the method for the production of the aforementioned compound, which has the following stages:

a. removing the Fmoc group from the amino group of TENTA GEL S RAM resin by shaking out with 20% solution of piperidine in DMF;

b. adding the ANB molecule to the earner prepared using the above-mentioned method;

c. in the next stage, attaching Fmoc-Arg(Pbf) to ANB-resin;

d. then removing the Fmoc group from the amino group Arg(Pbf)-ANB-resin using 20% solution of piperidine in DMF;

e. attaching Fmoc-Dap(Mtt) to the above-mentioned resin, using the standard procedure with HBTU and DIPEA (1:2);

f. in the next step, removing the Mtt group from Fmoc-Dap(Mtt)-Arg(Pbf)-ANB-resin using 2% TFA solution in methylene chloride (DCM) with 1% of triisopropylsilane, blending time: 15 minutes;

g. after this period of time, adding 3 drops of trifluoroacetic acid (TFA) to the resin sample; observing the appearance of a yellow colour—the colour appeared due to the presence of free Mtt groups;

h. repeating the procedure until the solution was colourless;

i. at the next stage, rinsing the resin three times with diisopropylethylamine solution in DMF (30%) and thus obtaining Fmoc-Dap-Arg(Pbf)-ANB-resin, to which PEG/DIPCI/HOBt solution in DMF/NMP (1:1, v/v) blend was then added;

j. performing the reaction of O2(Boc) residue acylation until the result of the Kaiser test was negative, which indicated that there were no free amino groups on the resin;

k. then removing the Fmoc group and attaching another Fmoc-Dap(Mtt) residue; the whole procedure was performed again while using different PEG residues—in the position no. 3 O1(Boc) was used, while in the position no. 4 O2(Cbz) was used;

l. completing synthesis of peptidomimetic by attaching the ABZ group;

m. removing the obtained peptidomimetic from the resin with simultaneous removing of the side casings from the resin, using TFA/phenol/triisopropylsilane/H$_2$O 88:5:2:5, v/v), obtaining ABZ-Dap(O2(Cbz))-Dap(O1) Dap(O2)Arg-ANB-NH$_2$.

The method where at stage b), before attaching the ANB to the solid carrier, resin with a free amino group was prepared by rinsing it three times in a 5% solution of N-methylmorpholine (NMM) in DMF, then in DMF (also three times), next, in a round-bottom flask, ANB was dissolved in 40 ml of DMF and HBTU, DMAP, and DIPEA, were added in sequence in the following molar ratio:

ANB:HBTU:DMAP:DIPEA (3:3:2:6). This solution was mixed with resin, and the reaction was performed for 3 hours; afterwards, the resin was drained under reduced pressure and rinsed. The procedure of attaching ANB to the polymere was repeated twice.

Method where at stage c) the process was commenced by dissolving the ninefold excess of the particular derivative in pyridine (22.2 ml) (for 1 g of peptidyl resin there are 10 ml of pyridine), then the mixture of amino acid in the pyridine was mixed with a portion of resin with sedimented 5-amino-2-nitrobenzoic acid; then it was cooled in an ice bath (prepared by mixing 1 part by weight of ice, 1 part by weight of NH$_4$Cl and 1 part by weight of NaNO$_3$) to the temperature of −15° C. Then the ninefold excess of phosphoryl chloride (POCl$_3$) was added, and the whole mixture was then stirred on a magnetic stirrer for 20 minutes. Then, the temperature of the reaction was brought to the room temperature for the next 30 minutes. Then, the flask with the mixture was placed in an oil bath and was heated for 6 hours in the temperature of 40° C. After the completion of the reaction, the resin with the first amino add residue attached was drained on a Schott funnel under reduced pressure; Then it was rinsed with methanol (MeOH) and chloromethane.

The subject of the invention is also the pharmaceutical solution for detecting cancer which contains an active substance and a buffer solution, where the new above-mentioned compound is the active substance and the buffer solution has the pH of 7-9.

The solution where TRIS HCl is the buffer solution.

The solution which detects cancer, in particular bladder cancer.

The subject of this invention is also the method of determining the presence of cancer, and it includes in vitro analysis of a human urine sample, to which a new compound, determined in claim 1, is added, and/or it incubates with the inhibitor of trypsic subunit PR671A.

The method, where in 1 minute, 60 minutes the measurement of the fluorescence intensity produced due to release of a fragment which contains the fluorescent tag ABZ-Dap(O2(Cbz))-Dap(O1)-Dap(O2)-Arg, is performed.

The method which detects cancer, particularly bladder cancer.

Furthermore, the subject of the invention is the cancer test kit, which detects bladder cancer positively, and contains the new compound, described above, and the inhibitor of trypsic subunit PR671A.

The use of hydrolysis of the new compound described above in position 5 by proteasome 20s for cancer detection, in particular bladder cancer.

The terms used above and in the description and patent claims have the following meaning:

ABZ—2-aminobenzoic acid
ANB—5-amino-2-nitrobenzoic acid
Dap—derivatives of diaminopropionic acids
DAPEG—the compound which contains Dap and PEG residues
PEG—functionalised mono-ethylene or diethylene glycol residues
DIPCI—diisopropylcarbodiimide
PEG=(O2(Cbz))-8-(benzyloxycarbonyl-amino)-3,6-dioxaoctanoic acid (O2(Cbz)).
O1(Boc)-(5-(t-butyloxycarhonyl-amino)-3-oxapentanoic add

The invention is illustrated by the following example of production, which does not limit it.

EXAMPLE

Synthesis of peptidodimetic ABZ-Dap(O2(Cbz))-Dap(O1)-Dap(O2)-Arg-ANB-NH$_2$

The synthesis of peptidodimetic ABZ-Dap(O2(Cbz))-Dap (O1)-Dap(O2)-Arg-ANB-NH$_2$, is divided into stages:
1) The first one is to remove the Fmoc group from the amino group of TENTA GEL S RAM resin through shaking out with 20% solution of piperidine in DMF. In the next step, the ANB (5-amino 2-nitrobenzoic acid) molecule is attached to the carrier prepared this way. Prior to attaching ANB to the solid carrier, the resin with the free amino group was prepared by rinsing it three times with 5% solution of N-methylmorpholine (NMM) in DMF, then in DMF (also three times), next, in a round-bottom flask, ANB was dissolved in 40 ml of DMF and HBTU, DMAP, and DIPEA were added in sequence in the following molar ratio:
ANB:HBTU:DMAP:DIPEA (3:3:2:6). This solution was mixed with resin, and the reaction was performed for 3 hours; afterwards, the resin was drained under reduced pressure and rinsed. The procedure of attaching ANB to the polymere was repeated twice.
2) In the next step, Fmoc-Arg(Pbf) was added to the ANB-resin. The process was commenced by dissolving the ninefold excess of the particular derivative in pyridine (22.2 ml) (for 1 g of peptidyl resin there are 10 ml of pyridine), then the mixture of the amino acid in pyridine was mixed with a portion of resin with sedimented 5-amino-2-nitrobenzoic acid; then it was cooled in an ice bath (prepared by mixing 1 part by weight of ice, 1 part by weight of NH$_4$Cl and 1 part by weight of NaNO$_3$) to the temperature of −15° C. Then ninefold excess of phosphoryl chloride (POCl$_3$) was added, and the whole mixture was then stirred on a magnetic stirrer for 20 minutes. Then, the reaction was brought to the room temperature for the next 30 minutes. Then the flask with the mixture was placed in an oil bath and heated for 6 hours in the temperature of 40° C. After the completion of the reaction, the resin with the first attached amino acid residue was drained on a Schott funnel under reduced pressure. Then it was rinsed with methanol (MeOH) and chloromethane.
Then the Fmoc group was removed from the amino group Arg(Pbf)-ANB-resin using 20% solution of piperidine in the DMF.
3) Fmoc-Dap(Mtt) was then attached to the above-mentioned resin, using the standard procedure with HBTU and DIPEA (1:2). In the next step, the Mtt group was removed from Fmoc-Dap(Mtt)-Arg(Pbf)-ANB-resin using the 2% TFA solution in methylene chloride (DCM) with 1% of triisopropylsilane, blending time: 15 minutes, after this period of time, 3 drops of trifluoroacetic acid (TFA) were added to the resin sample; the appearance of a yellow colour was Observed—the colour appeared due to the presence of free Mtt groups. The procedure was repeated until the solution was colourless.
4) At the next stage, the resin was rinsed three times with the diisopropylethylamine solution in DMF (30%) and thus Fmoc-Dap-Arg(Pbf)-ANB-resin was obtained, to which the PEG/DIPCI/HOBt solution in the DMF/NMP (1:1, v/v) mixture was then added, where DIPCI stands for diisopropylcarbodiimide and PEG is 8-(tert-butyloksyl-amino)-3,6-dioxaoctanoic acid (O2(Boc). The reaction of residue acylation was performed until the result of the Kaiser test was negative, which indicated that there were no free amino groups on the resin. Then, the Fmoc group was removed and another Fmoc-Dap(Mtt) residue was attached; the whole procedure was performed again while using different PEG residues—in the position no. 3 O1(Boc) was used, while in the position no. 4 O2(Cbz) was used.
5) the synthesis of the peptidomimetic was completed by attaching the ABZ group.

The obtained peptidomimetic was then removed from the resin with simultaneous removing of the side casings from the resin, using TFA/phenol/triisopropylsilane/H2O 88:5:2:5, v/v), obtaining ABZ-Dap(O2(Cbz))-Dap(O1)-Dap(O2) Arg-ANB-NH$_2$.

New Compound Identity/Characteristics

Figure 5:
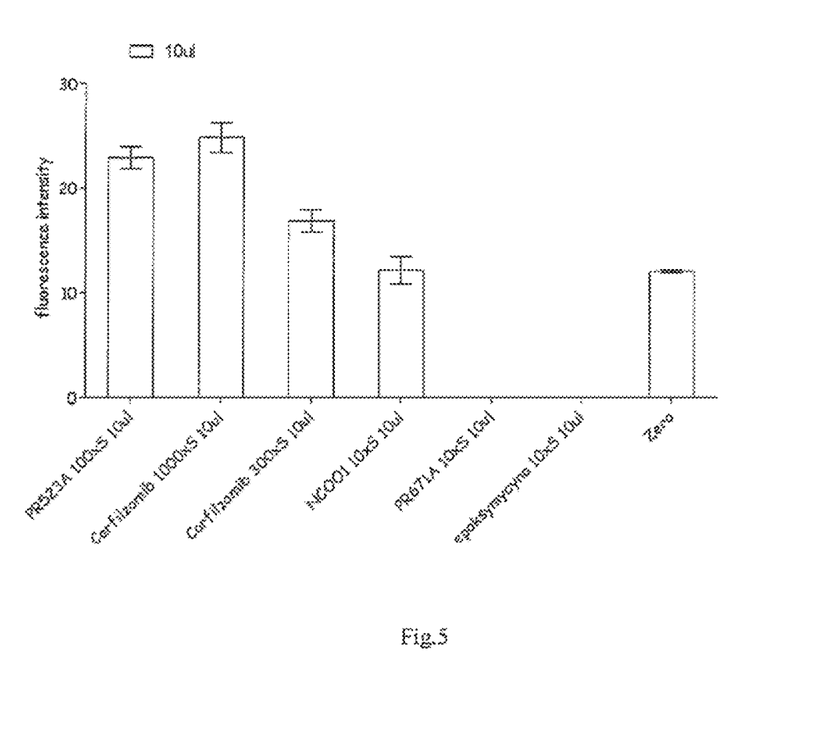
FIG. 5—it presents the influence of the inhibitors on the level of hydrolysis of the compound, where PR523A—carfilzomib, inhibitor of chymotrypsin-like proteasome 20S subunit, NCOO1 inhibitor of caspase-like subunit of proteasome 20S, PR671A inhibitor of trypsin-like subunit of proteasome 20S, epoxomiein inhibitor of all the three activities of proteasome 20S.

The obtained compound undergoes a selective hydrolysis by the human trypsin subunit of proteasome 20S. The results of the experiment in which the obtained compound was incubated with proteasome 20S with selectively blocked enzyme subunits as: PR523A, carfilzomib selective chymotrypsin subunits inhibitors, NCOO1 selective caspore subunit inhibitor, and PR671A trypsin subunit inhibitor—all clearly indicate that there is no hydrolysis of the compound (no fluorescence growth) for the system only when the PR671A inhibitor is used (FIG. 5). Moreover, lack of activity of proteasome incubated in the presence of epoxomicin (inhibitor of all the three units) confirms that the elaborated compound is hydrolysed by proteasome 20S.

Figure 6:
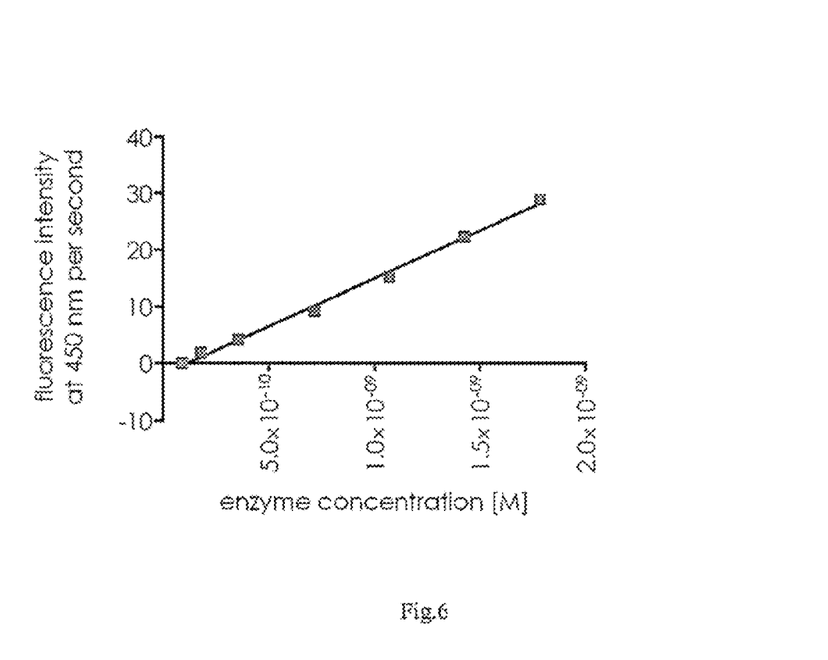
FIG. 6—it presents the titration curve of the compound by reducing the concentration of proteasome 20S. The obtained limit of detection was $10^{-11}$ M, which corresponds to $5\times10^{-16}$ g.

Tirating the obtained compound with decreasing amounts of proteasome 20S (FIG. 6) indicates that a noticeable growth of fluorescence (signal to noise ratio is 3:1) is observed at the concentration of 10 pM, which is $5 \times 10^{-16}$ g of proteasome in the probe.

Figure 7:
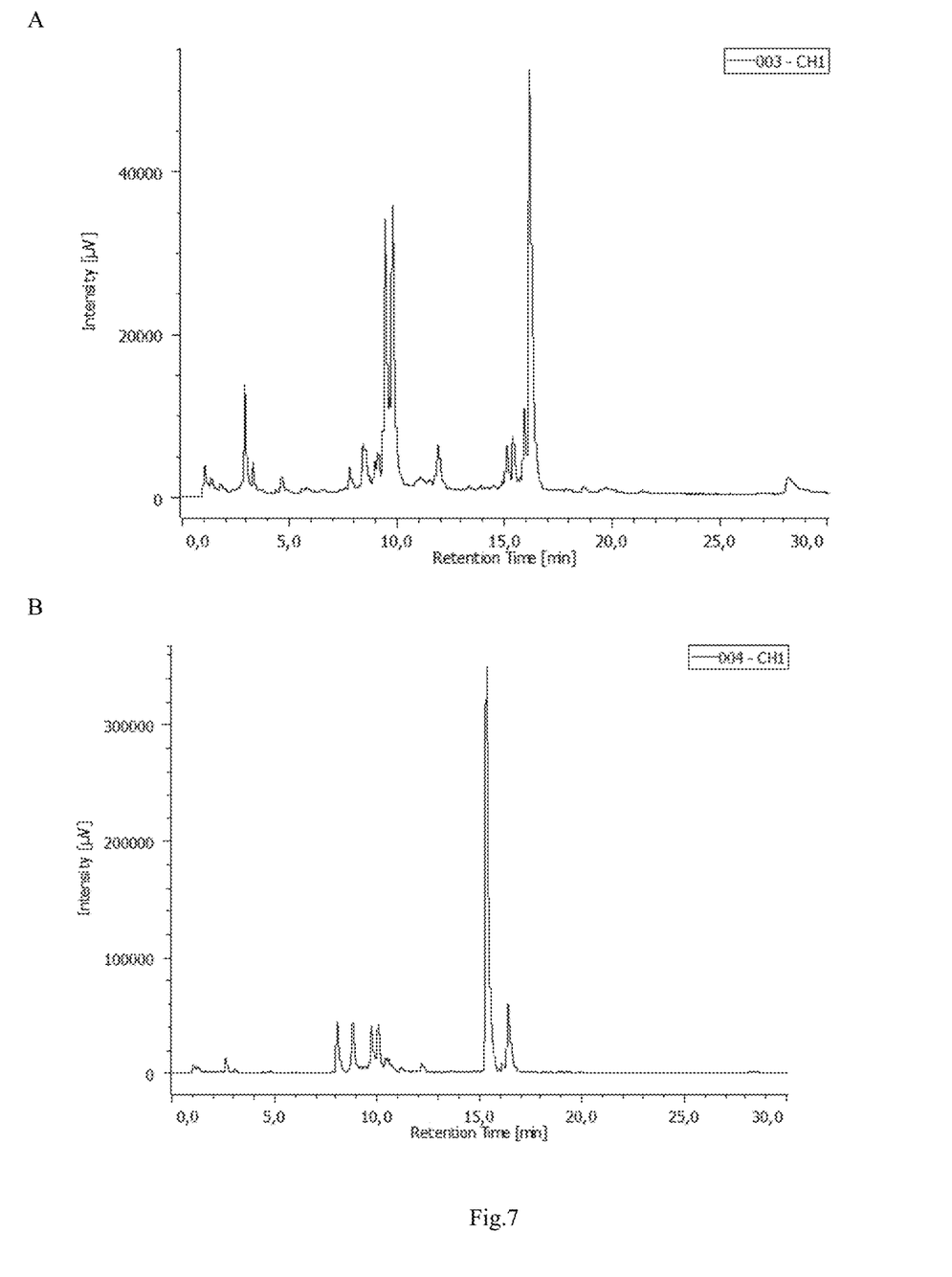
FIG. 7—it presents the hydrolysis of the ABZ-Dap(O2(Cbz))-Dap(O1)-Dap(O2)-Arg-ANB-NH2 compound in the presence of proteasome 20S. Time A) 1 minute B) 60 minutes. Peak with retention time of 16.15 is the ABZ-Dap(Cbz)-Dap(O)1-Dap(Cbz)-Arg-ANB-NH$_2$ compound, peak with retention time of 15.23 is a fragment of ABZ-Dap(Cbz)-Dap(O1)-Dap(Cbz)-Arg-OH.
Figure 8:
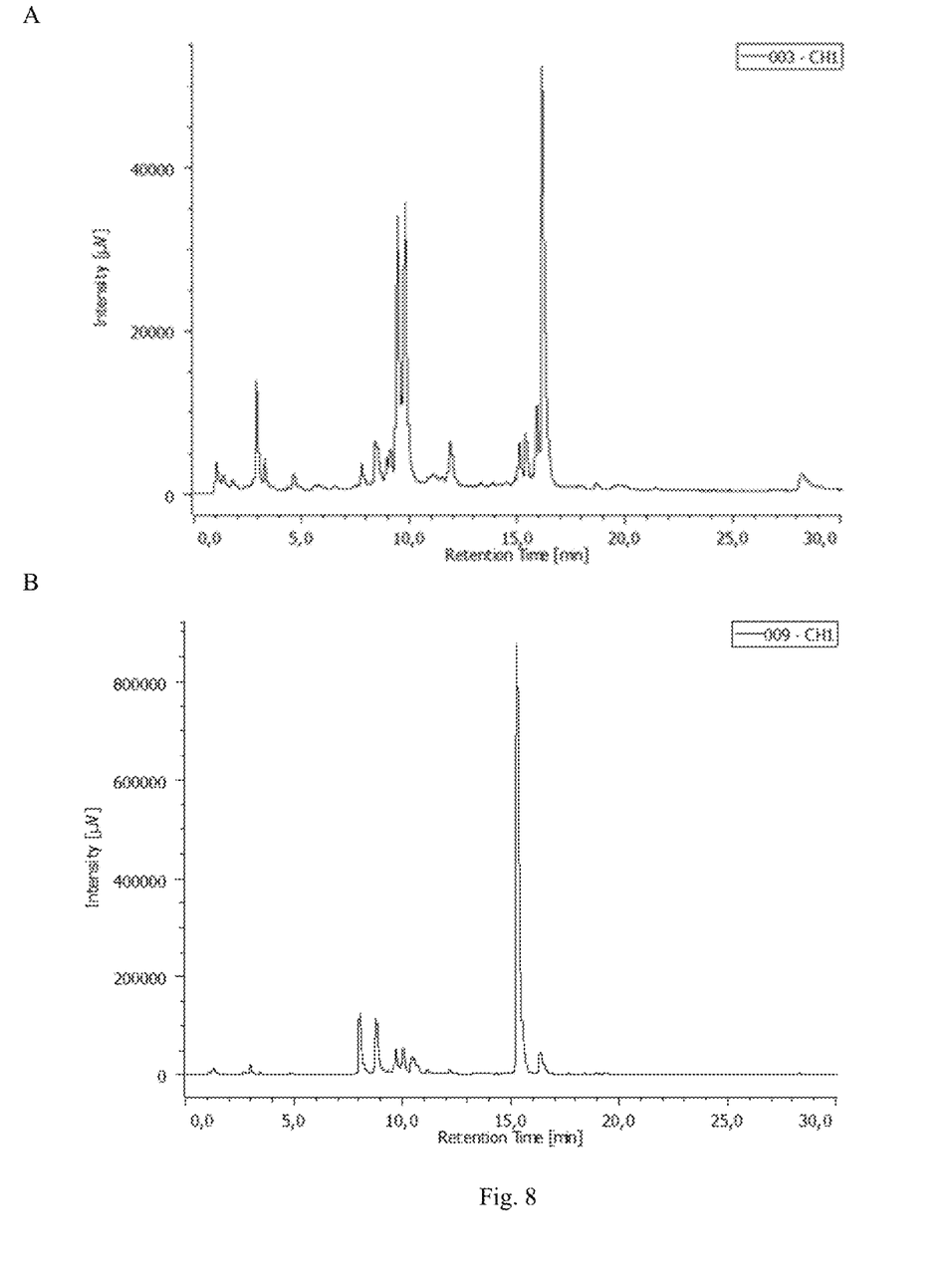
FIG. 8—it presents the hydrolysis of the ABZ-Dap(O2(Cbz))-Dap(O1)-Dap(O2)-Arg-ANB-NH2 compound in human urine (A) healthy (B) diagnosed with bladder cancer. Peak with retention time of 16.15 is an ABZ-Dap(O2(Cbz))-Dap(O1)-Dap(O2)-Arg-ANB-NH2 compound, peak with a retention time of 15.23 is a fragment of ABZ-Dap (O2Cbz)-Dap(O1)-Dap(O2)-Arg-OH.

FIG. 7 illustrates (A) a HPLC RP analysis of the obtained compound, with the signals at about $10^{th}$ minute coming from the buffer ingredient (buffer is 50 mM TRIS-HCl pH 8.2 with 0.02% of SDS (sodium dodecyl sulphate), where (B) HPLC RP analysis of the incubated compound in the presence of commercially available human proteasome 20S for 60 minutes was used. FIG. 8, illustrates a similar analysis, but healthy human urine samples (A) and urine samples of a patient diagnosed with bladder cancer (B) replaced proteasome 20S. The analysis of both figures clearly indicates that the obtained compound, when exposed to human proteasome 20S, decomposes into two fragments ANB-NH2 and fluorescent ABZ-Dap(O2(Cbz)-Dap(O1)-Dap(O2)-Arg-OH.

Figure 9:
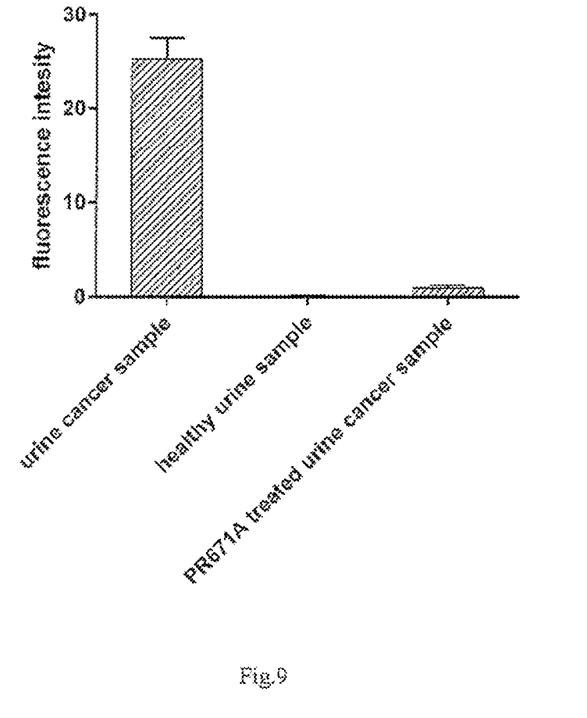
FIG. 9—it presents the influence of the inhibitors on the hydrolysis of the compound by the urine sample with cancer diagnosis.
Figure 10:
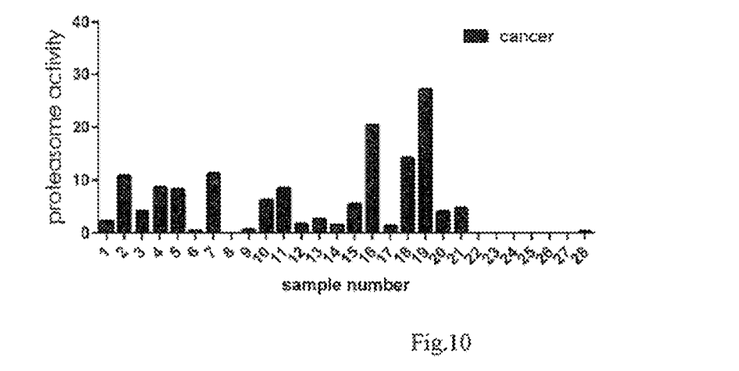
FIG. 10—it presents the preliminary diagnosis of bladder cancer. Samples 1-21 are taken from patients diagnosed with bladder cancer. 22-28 are control samples taken from healthy patients.

This is confirmed by FIG. 9, where the probe from FIGS. 8B (bladder cancer) and 8A (cancer-free) was analysed, and 8B incubated with trypsin subunit inhibitor PR671A. The results obtained clearly indicate that there is no decomposition of the analysed compound in a healthy patient's urine, whereas in the urine of a patient diagnosed with cancer the compound decomposes. Furthermore, this decomposition is hindered by selective trypsin subunit inhibitor.

During the next stage, 21 samples of urine from patients diagnosed with bladder cancer, and 8 cancer-free samples were analysed. The results of such an analysis indicate that the fluorescence grew in 20 out of 21 samples with urine of patients diagnosed with bladder cancer.

Figure 11:
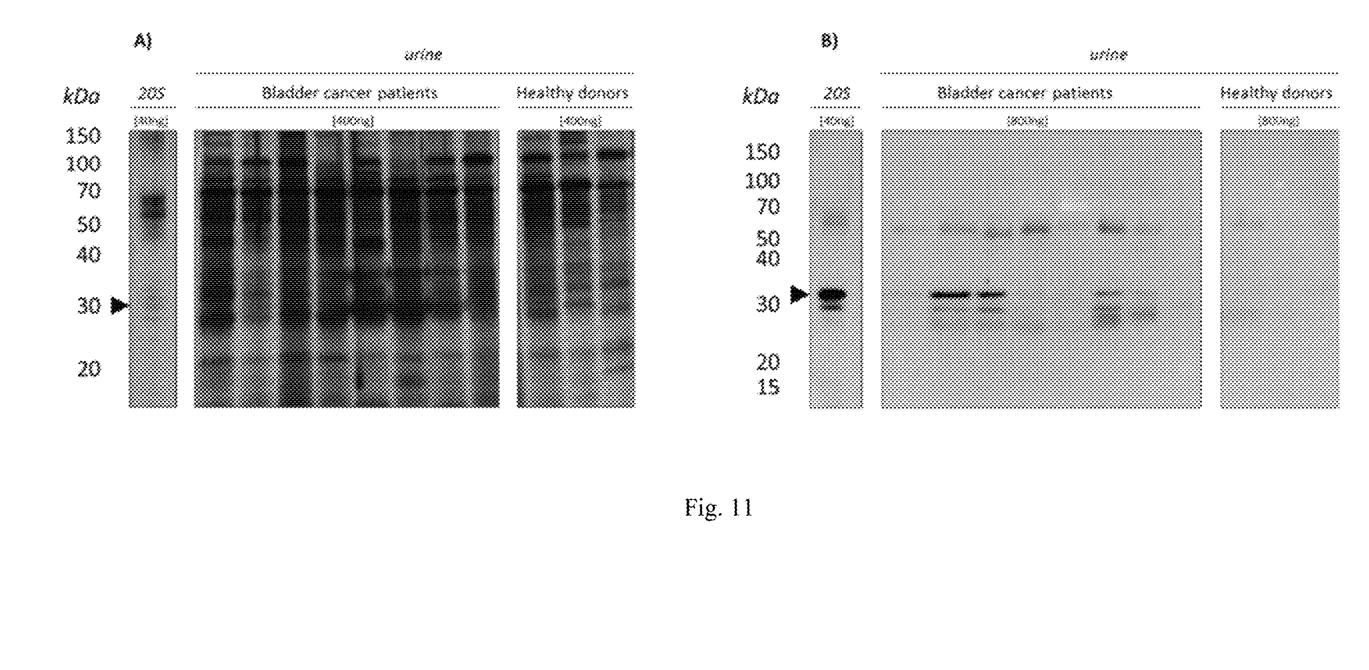
FIG. 11—it presents the SDS PAGE gel, coloured with silver (A) Western blot analysis (B) of samples taken from healthy patients (22-24) and patients with cancer (2,5,8,10, 14,16,20,21). Murine monoclonal antibody anti-20S IgG1 was used as the primary antibody, and IgG-HRP rabbit anti-mouse antibody as the secondary one. The signal was obtained by using the chemiluminescent substrate.

Selected samples were analysed using immunochemical techniques (Western blot), where proteasome 20S was subject to detection. FIG. 11 indicates that the positive response (die presence of proteasome) was obtained for all samples taken from patients diagnosed with cancer, whereas in healthy patients, this enzyme was not found.

LITERATURE

1. Borissenko L., Groll M., Diversity of proteasomal missions: fine tuning of the immune response, Biol. Chem., 388, 947-955, 2007.
2. Groll M., Bochtler M., Brandstetter H., Clausen T., Huber R., Molecular machines for protein degradation, ChemBioChem., 6, 222-256, 2005.
3. Ma W, Kantazjian H, O'Brien S, Jilani I, Zhang X, Estrov Z, et al. Enzymatic activity of circulating proteasomes correlates with clinical behavior in patients with chronic lymphocytic leukemia. Cancer 2008; 112:1306-12.
4. Ostrowska H, Hempel D, Holub M, Sokolowski J, Kloczko J. Assessment of circulating proteasome chymotrypsin-like activity in plasma of patients with acute and chronic leukemias. Clin Biochem. 2008 November; 41(16-17):1377-83
5. www.promega.com
6. Ma W, Kantarjian H, O'Brien S, Jilani I, Zhang X, Estrov Z, et al. Enzymatic activity of circulating proteasomes correlates with clinical behavior in patients with chronic lymphocytic leukemia. Cancer 2008; 112:1306-12.

The invention claimed is:
1. A compound of the following chemical formula:

where:
ABZ stands for 2-aminobenzoic acid;
DAP stands for diaminopropanoic acid (Dap) derivatives, modified by functionalised residues of mono-ethylene or diethylene glycol (PEG); and
ANB stands for 5-amino-2-nitrobenzoic acid.
2. A method for the production of the compound of claim 1, the method comprising the following steps:
n. removing the Fmoc group from amino group of TENT A GEL S RAM resin through shaking out with 20% solution of piperidine in DMF to prepare a carrier;
o. adding the ANB molecule to the carrier prepared in step n to prepare an ANB-resin;
p. attaching Fmoc-Arg(Pbf) to the ANB-resin;
q. removing the Fmoc group to provide an Arg(Pbf)-ANB-resin using 20% solution of piperidine in DMF;
r. attaching Fmoc-Dap(Mtt) to the Arg(Pbf)-ANB-resin, using HBTU and DIPEA (1:2), to prepare the Fmoc-Dap(Mtt)-Arg(Pbf)-ANB-resin;
s. removing the Mtt group from the Fmoc-Dap(Mtt)-Arg(Pbf)-ANB-resin using 2% TFA solution in methylene chloride (DCM) with 1% of triisopropylsilane, wherein the blending time is 15 minutes;
t. after this period of time from step s, adding 3 drops of trifluoroacetic acid (TFA) to the resin sample, wherein the appearance of a yellow colour was observed—the colour appeared due to the presence of free Mtt groups;
u. repeating the procedure from step t until the solution was colourless;
v. rinsing the resin from step u three times with diisopropylethylamine solution in DMF (30%) to obtain an Fmoc-Dap-Arg(Pbf)-ANB-resin, to which PEG/DIPCI/HOBt solution in DMF/NMP (1:1, v/v) blend was then added;
w. performing the reaction of O2(Boc) residue acylation until the result of a Kaiser test was negative, which indicated that there were no free amino groups on the resin;
x. removing the Fmoc group and attaching another Fmoc-Dap(Mtt) residue; performing steps n to x again while using different PEG residues—in the position no. 3 O1 (Boc) was used, while in the position no. 4 O2(Cbz) was used;
y. attaching the ABZ group so the synthesis of a peptidomimetic was completed;
z. removing the peptidomimetic obtained in step y from the resin with simultaneous removing of the side casings from the resin, using TFA/phenol/triisopropylsilane/$H_2O$ 88:5:2:5, v/v), thereby obtaining ABZ-Dap(O2(Cbz))-Dap(O1)-Dap(O2)Arg-ANB-$NH_2$.
3. The method according to claim 2, further comprising the following steps:
i) prior to step o, the resin with the free amino group was prepared by rinsing it three times with 5% solution of N-methylmorpholine (NMM) in DMF, and then in DMF (also three times),
ii) next, in a round-bottom flask, ANB was dissolved in 40 ml of DMF and HBTU, DMAP, and DIPEA were added in sequence in the following molar ratio: ANB:HBTU:DMAP:DIPEA (3:3:2:6) to prepare a solution;
iii) the solution was mixed with resin, and the reaction was performed for 3 hours;
iv) the resin was drained under reduced pressure and rinsed; and
v) the procedure of attaching ANB to the polymer was repeated twice.
4. The method according to claim 2, further comprising the following steps:
i) wherein step p was commenced by dissolving ninefold excess of the particular derivative in pyridine (22.2 ml) (for 1 g of peptidyl resin there are 10 ml of pyridine);
ii) the mixture of amino acid in pyridine was mixed with a portion of resin with sedimented 5-amino-2-nitrobenzoic acid;
iii) the mixture from step ii) was cooled in an ice bath (prepared by mixing 1 part by weight of ice, 1 part by weight of $NH_4Cl$ and 1 part by weight of $NaNO_3$) to the temperature of −15° C.;
iv) ninefold excess of phosphoryl chloride ($POCl_3$) was added, and the whole mixture was then stirred on a magnetic stirrer for 20 minutes;
v) the mixture from step iv) was brought to the room temperature for the next 30 minutes;
vi) the flask with the mixture from step v) was placed in an oil bath and it was heated for 6 hours in the temperature of 40° C.;
vii) after the completion of the reaction from step vi), the resin with the first attached amino acid residue was drained on a Schott funnel under reduced pressure; and
viii) the resin was rinsed with methanol (MeOH) and dichloromethane.

5. A pharmaceutical solution for cancer detection, wherein the solution comprises an active substance and a buffer, wherein the active substance is contained in the compound of claim 1, and the buffer has the pH of 7-9.

6. The pharmaceutical solution according to claim 5, wherein the buffer is TRIS HCl.

7. The pharmaceutical solution according to claim 5, wherein the cancer is bladder cancer.

8. A method for determining the presence of cancer, wherein the method comprises in vitro analysis of a human urine sample, to which the compound of claim 1 is added and is incubated with the inhibitor of trypsic subunit PR671 A.

9. The method according to claim 8, wherein at 1 minute and at 60 minutes the measurement of the fluorescence produced due to disengagement of a fragment which contains the fluorescent tag ABZ-Dap(O2(Cbz))-Dap(O1)-Dap (O2)-Arg, is performed.

10. The method according to claim 8, wherein the cancer is bladder cancer.

11. A test kit which detects bladder cancer, wherein the test kit comprises the compound of claim 1 and an inhibitor of the trypsic subunit PR671A.

12. The test kit of claim 11, wherein hydrolysis hydrolysis of position 5 of the compound of claim 1 by proteasome 20s detects bladder cancer.

* * * * *